United States Patent [19]

Herve et al.

[11] 4,357,350
[45] Nov. 2, 1982

[54] NOVEL ACARICIDE COMPOSITIONS

[75] Inventors: Jean J. Herve, Aubagne; Serge Smolikowski, Marseilles, both of France

[73] Assignee: Roussel Uclaf, Paris, France

[21] Appl. No.: 35,811

[22] Filed: May 4, 1979

Related U.S. Application Data

[63] Continuation of Ser. No. 906,752, May 17, 1978, abandoned.

[51] Int. Cl.³ .................... A01N 37/34; A01N 31/04
[52] U.S. Cl. .................................... 424/304; 424/345
[58] Field of Search ..................... 424/304, 306, 345

[56] References Cited

U.S. PATENT DOCUMENTS 2,812,280  11/1957  Wilson et al. ..................... 424/345
3,102,070   8/1963  Riley et al. ....................... 424/345
3,835,176   9/1974  Matsuo et al. ................ 424/304 X
3,839,562  10/1974  Chodnekan et al. ............. 424/306
3,899,586   8/1975  Okuno et al. ................. 424/306 X
3,973,036   8/1976  Hirano et al. ..................... 424/304

*Primary Examiner*—Douglas W. Robinson
*Attorney, Agent, or Firm*—Hammond & Littell, Weissenberger and Muserlian

[57] ABSTRACT

Novel acaricide compositions containing as the active ingredient, a synergistic mixture of (S)α-cyano-3-phenoxy-benzyl 1R, cis 2,2-dimethyl-3-(2',2'-dibromovinyl)-cyclopropane-1-carboxylate and either 2,2,2-trichloro-1,1-di-(4-chlorophenyl)-ethanol or a mixed anhydride of benzoic acid and 3-chloro-2,6-dimethoxy-N-ethoxy-benzenecarboximidic acid and to a novel method of combatting acariens.

11 Claims, No Drawings

NOVEL ACARICIDE COMPOSITIONS

PRIOR APPLICATION

This application is a continuation of our commonly assigned, copending U.S. application Ser. No. 906,752 filed May 17, 1978, now abandoned.

OBJECTS OF THE INVENTION

It is an object of the invention to provide acaricide compositions having a synergistic activity.

It is a further object of the invention to provide an improved method of combatting acariens.

These and other objects and advantages of the invention will become obvious from the following detailed description.

THE INVENTION

The novel acaricidal compositions of the invention are comprised of an acaricidal amount of a synergistic mixture of (S)α-cyano-3-phenoxy-benzyl 1R, cis 2,2-dimethyl-3-(2',2'-dibromovinyl)-cyclopropane-1-carboxylate and either 2,2,2-trichloro-1,1,-di-(4-chlorophenyl)-ethanol or a mixed anhydride of benzoic acid and 3-chloro-2,6-dimethoxy-N-ethoxybenzenecarboximidic acid and preferably an inert carrier.

The said 3 components of the novel compositions are known compounds having acaricidal activity but it has been unexpectedly discovered that the claimed compositions have a clear synergistic activity against acariens which are vegetable parasites such as *Panonychus Ulmi* which attack vines and *Tetranychus Urticae* which attack beans. Tests have shown that the acaricidal effects of the claimed compositions are greater than the sum of the activity of the components individually.

The compositions of the invention have a great economical interest since very satisfactory acaricidal results are obtained with the compositions of the invention at doses at which the individual components are ineffective and therefore less of the active compound is required.

The compositions are generally effective against acarien parasites that attack vegetables such as *Panonychus Ulmi, Tetranychus Urticae, Tetranychus Cinnabarrinus, Tetranychus Atlanticus, Eotetranychus Carpini* and *Bryobia Rubrioculus.*

Among the preferred compositions of the invention are composition α containing 1 to 100 parts by weight of (S)α-cyano-3-phenoxy-benzyl 1R, cis 2,2-dimethyl-3-(2',2'-dibromovinyl)-cyclopropane-1-carboxylate per 100 parts by weight of 2,2,2-trichloro-1,1-di-(4-chlorophenyl)-ethanol and composition β containing 1.5 to 50 parts by weight of (S)α-cyano-3-phenoxy-benzyl 1R, cis 2,2-dimethyl-3-(2',2'-dibromovinyl)-cyclopropane-1-carboxylate per 100 parts by weight of the mixed anhydride of benzoic acid and 3-chloro-2,6-dimethoxy-N-ethoxy-benzenecarboximidic acid.

The compositions of the invention may be in the form of powders, granules, suspensions, emulsions and solutions containing besides the active ingredients, other ingredients such as cationic, anionic or nonionic surface active agents, inert powders such as talc, clays, silicates or kieselguhr, a vehicle such as water, alcohol, hydrocarbons or other organic solvents or animal, vegetable or mineral oil.

The novel method of the invention for combatting acariens comprises contacting acariens with an acaricidally effect amount of composition α or composition β.

The usual total effective dose for composition α is 10 to 1000 g per hectare and for composition β is 150 to 350 g per hectare.

Among preferred compositions of the invention are the compositions $α_1$ containing 1.25 to 25, most preferably 4.5 to 8.5, parts by weight of (S)α-cyano-3-phenoxy-benzyl 1R, cis 2,2-dimethyl-3-(2',2'-dibromovinyl)-cyclopropane-1-carboxylate per 100 parts of 2,2,2-trichloro-1,1-di-(4-chlorophenyl)-ethanol and the said compositions are especially effective against the Panonychus species at a dose of 200 to 450 g per hectare. The said compositions may be applied at a rate of 5 to 50 g of the said (S)α-cyano-3-phenoxybenzyl ester and 200 to 400 g of the said substituted ethanol per hectare.

Another preferred composition of the invention which has been found to be particularly useful against Tetranychus species are the compositions $α_2$ containing 10 to 75, most preferably 25 to 50, parts by weight of (S)α-cyano-3-phenoxy-benzyl 1R, cis 2,2-dimethyl-3-(2',2'-dibromovinyl)-cyclopropane-1-carboxylate per 100 parts by weight of 2,2,2-trichloro-1,1-di-(4-chlorophenyl)-ethanol and the said compositions are applied at a total dose of 15 to 500 g per hectare. This corresponds to a dose of 5 to 25 g of the (S)α-cyano-3-phenoxy-benzyl ester and 100 to 300 g of the said substituted ethanol per hectare.

A further preferred composition of the invention which has been found to be particularly useful against Panonychus species are the compositions $β_1$ containing 4 to 16 parts by weight of (S)α-cyano-3-phenoxy-benzyl 1R cis 2,2-dimethyl-3-(2',2'-dibromovinyl)-cyclopropane-1-carboxylate per 100 parts by weight of the mixed anhydride of benzoic acid and 3-chloro-2,6-dimethoxy-N-ethoxy-benzenecarboximidic acid and the said compositions are applied at a total dose of 100 to 350 per hectare. This dosage corresponds to a dosage of 10 to 25 g of the said (S)α-cyano-3-phenoxy-benzyl ester and 100 to 200 g of the said mixed anhydride per hectare.

In the following examples, there are described several preferred embodiments to illustrate the invention. However, it should be understood that the invention is not intended to be limited to the specific embodiments.

EXAMPLE 1

An acaricide composition was prepared containing 355 g/l of technical 2,2,2-trichloro-1,1-di-(4-chlorophenyl)-ethanol, 12.75 g/l of technical (S)α-cyano-3-phenoxy-benzyl 1R, cis 2,2-dimethyl-3-(2',2'-dibromovinyl)-cyclopropane-1-carboxylate, 5 g/l of 2,6-di-tert.-butyl-p-cresol, 80 g/l of Emcol AK 18-35 and 580 g/l of xylene. Emcol AK 18-35 is a strong hydrophile emulsifier sold by the firm Witco-chemical

EXAMPLE 2

An acaricide composition was prepared containing 355 g/l of 2,2,2-trichloro-1,1-di-(4-chlorophenyl)-ethanol, 25.5 g/l of (S)α-cyano-3-phenoxy-benzyl 1R, cis 2,2-dimethyl-3-(2',2'-dibromovinyl)-cyclopropane-1-carboxylate, 10 g/l of 2,6-di-tert.-butyl-p-cresol, 80 g/l of Emcol AK 18-35, and 567.2 g/l of xylene.

EXAMPLE 3

An acaricide composition was prepared containing 216 g/l of technical mixed anhydride of benzoic acid and 3-chloro-2,6-dimethoxy-N-ethoxy-benzenecarboximidic acid, 12.75 g/l of (S)α-cyano-3-phenoxy-benzyl 1R, cis 2,2-dimethyl-3-(2',2'-dibromovinyl)-cyclopropane-1-carboxylate, 5 g/l of 2,6-di-tert.-butyl-p-cresol, 35 g/l of Emcol H 300 B, 25 g/l of Emcol H 500 B and 652.9 g/l of xylene. The 2 Emcol products are mixtures of polyoxyethylene ether and calcium alkylbenzenesulfonates.

EXAMPLE 4

An acaricide composition was prepared containing 216 g/l of technical mixed anhydride of benzoic acid and 3-chloro-2,6-dimethoxy-N-ethoxy-benzenecarboximidic acid, 25.5 g/l of (S)α-cyano-3-phenoxy-benzyl 1R, cis 2,2-dimethyl-3-(2',2'-dibromovinyl)-cyclopropane-1-carboxylate, 16 g/l of 2,6-di-tert.-butyl-p-cresol, 35 g/l of Emcol H 300 B and 25 g/l of Emcol H 500 B.

EXAMPLE 5

The effectiveness of (S)α-cyano-3-phenoxy-benzyl 1R, cis 2,2-dimethyl-3-(2',2'-dibromovinyl)-cyclopropane-1-carboxylate (compound A) and 2,2,2-trichloro-1,1-di-(4-chlorophenyl)-ethanol (compound B) and mixtures thereof was determined against *Panonychus Ulmi* using vines of the Sirah variety. The test was repeated 4 times for each dose using the block method with an untreated control in each block. Each elementary block consisted of 10 vines and a single treatment was effected with a base of 1000 liters of spray mixture per hectare using a Van der Weij sprayer at a constant pressure. Reading were taken 7 days after the treatment to determine the number of moving forms (larvae and adults) present on 15 leaves which were collected by brushing of the leaves and the results were reported in a percentage of reduction of the population as compared to the non-treated controls. The comparison used emulsifiable concentrates containing 1.25, 2.5 and 5 g per hectoliter of compound A, emulsifiable concentrates containing 30 g/hl of compound B and mixtures prepared just before use of emulsifiable concentrates containing 30 g/hl of compound B and 1.25, 2.5 or 5 g of compound B.

To show more clearly the synergistic effect, the Limpel formula was used which permitted the evaluation of theoretical efficacity to be obtained with the combinations. Efficacity (E) of the association of $P_1+P_2$ at dosages $D_1+D_2$ is expressed with the percentage of efficacity (X) obtained with product $P_1$ at a dose $D_1$ and with the percentage of efficacity (Y) obtained with product $P_2$ at dose $D_2$ or $$E = X + Y - XY/100$$

The experimental results and expected efficacity is reported in Table I.

TABLE I

| Compound | Dose in g/hl | % Reduction of population of 7 days after Treatment | |
|---|---|---|---|
| | | Obtained | Expected* |
| A | 1.25 | 38.6 | |
| | 2.5 | 41.7 | |
| | 5.0 | 50.0 | |
| B | 30 | 20.1 | |
| A+B | 1.25+30 | 80.5 | 51 |
| A+B | 2.5+30 | 65.4 | 53.4 |
| Controls | | 492** | |

*Limpel method
**Number living on 15 leaves

The results of Table I clearly show the synergistic effect obtained by the combination of compounds A and B.

EXAMPLE 6

The activity against *Tetranychus Urticae* was determined for compounds A and B using bean plants having 2 bell leaves which were sprayed with 4 ml of the test compounds equally on the 2 faces of each border. Before the spraying, a band of glue was placed at the joint of convergence of two petioles to prevent the escape of acariens. After the treatment, 25 adult *Tetranychus Urticae* were placed on each leaf and 48 hours later the degree of mortality was determined. 9 days after the treatment, the degree of ovicidal effect (% of eggs not opened) and the larvicidal effect (% of mortality) was determined for the compounds. Two tests were used for each dose and the results are reported in Table II as a percent of mortality and in Table II as a percent of reduction calculated as follows:

% reduction = $(N_1 - N_F)/N_1 \times 100$ wherein $N_1$ is the initial number of adults and $N_F$ is the final number of living larvae and if $N_F > N_1$, the percentage is 0.

TABLE II

| | Compound A | | |
|---|---|---|---|
| Compound B | 0 | 0.625 g/hl | 1.25 g/hl |
| 0 | (1) 0.0 | 2.4 | 9.0 |
| | (2) 1.4 | 0.7 | 37.8 |
| | (3) 1.3 | 0.7 | 10.1 |
| | 59.8 | 73.4 | 80.0 |
| 1.25 g/hl | 18.8 | 88.0 | 86.0 |
| | 8.7 | 8.7 | 16.7 |
| | 100 | 95.8 | 100 |
| 2.50 g/hl | 37.5 | 93.0 | 88.3 |
| | 30.0 | 11.1 | 20.0 |
| | 100 | | |
| 5.0 g/hl | 62.2 | | |
| | 58.1 | | |

(1) % of dead adults
(2) % of closed eggs
(3) % of dead larvae

TABLE III

| | Compound A | | |
|---|---|---|---|
| Compound B | 0 | 0.625 g/hl | 1.25 g/hl |
| 0 | 0 | 0 | 0 |
| 1.25 g/hl | 0 | 73.4 | 94.7 |
| 2.50 g/hl | 91.1 | 88.7 | 77.1 |
| 5.00 g/hl | 83.3 | — | — |

The two Tables show the synergistic effect with Table III most clearly showing the synergism of compounds A and B. For example, at a dose of 0.625 g/hl, compound A does not have any effect on the reduction of the population and neither does compound B at a dose of 1.25 g/hl. However, at combined dosage of 0.625 g/hl of compound A and 1.25 g/hl of compound B, a 73.4% reduction of the population is obtained.

To show the synergism in another manner, the Limpel formula was used to determine the theoretically expected efficacity of the association and the results are compared with the returned results in Table IV.

TABLE IV

| | Compound A | | |
|---|---|---|---|
| Compound B | 0 | 0.625 g/hl | 1.25 g/hl |

TABLE IV-continued

|  |  |  | Actual | Expected | Actual | Expected |
|---|---|---|---|---|---|---|
| 0 | 0.0 |  | 2.4 |  | 9.0 |  |
|  | 1.4 |  | 0.7 |  | 37.8 |  |
|  | 1.3 |  | 0.7 |  | 10.1 |  |
| 1.25 g/hl | 59.8 | 73.4 | 60.8 | 80.0 | 63.4 |  |
|  | 18.8 | 88.0 | 19.4 | 86.0 | 49.5 |  |
|  | 8.7 | 8.7 | 9.3 | 16.7 | 17.9 |  |
|  | 100 | 95.8 | 100 | 100 | 100 |  |
| 2.5 g/hl | 37.5 | 93.0 | 37.9 | 88.3 | 61.1 |  |
|  | 30.0 | 11.1 | 30.5 | 20.0 | 37.1 |  |

The results of this test show the net synergistic effect with compounds A and B. The larvicide effect is weak but they have an elevated percentage of mortality with adults and eggs and the final reduction of population is very high.

EXAMPLE 7

The acaricide activity against *Panonychus Ulmi* was determined for compound A and the mixed anhydride of benzoic acid and 3-chloro-2,6-dimethoxy-N-ethoxy-benzenecarboximidic acid (compound C) was determined as in Example 5 and the results are reported in Table V.

TABLE V

| Compound | Doses in g/hl | % Reduction of Population 7 days after treatment | |
|---|---|---|---|
|  |  | obtained | expected* |
|  | 1.25 | 38.6 | — |
| A | 2.50 | 41.7 | — |
|  | 5.00 | 50.0 | — |
| C | 20.0 | 39.9 |  |
| A + C | 1.25 + 20 | 71.5 | 63.1 |
|  | 2.50 + 20 | 70.7 | 65 |
| Control** |  | 492 |  |

*Limpel formula
**Number of living forms on 15 leaves

The results of Table V clearly show the net synergistic effect of the combination of compounds A and C.

Various modifications of the compositions and method of the invention may be made without departing from the spirit or scope thereof, and it is to be understood that the invention is intended to be limited only as defined in the appended claims.

We claim:

1. An acaricidal composition comprising an acaricidally effective amount of a synergistic mixture of 1 to 100 parts by weight of (S)α-cyano-3-phenoxy-benzyl 1R, cis 2,2-dimethyl-3-(2',2'-dibromovinyl)-cyclopropane-1-carboxylate and 100 parts by weight of 2,2,2-trichloro-1,1-di-(4-chlorophenyl)-ethanol and an inert carrier.

2. A composition of claim 1 wherein the amount of the said (S)α-cyano-3-phenoxy-benzyl ester is 1.25 to 25 parts by weight.

3. A composition of claim 1 wherein the amount of the said (S)α-cyano-3-phenoxy-benzyl ester is 4.5 to 8.5 parts by weight.

4. A composition of claim 1 wherein the amount of the said (S)α-cyano-3-phenoxy-benzyl ester is 10 to 75 parts by weight.

5. A composition of claim 4 wherein the amount of the said (S)α-cyano-3-phenoxy-benzyl ester is 25 to 50 parts by weight.

6. A method of combatting acariens comprising contacting the acariens with an acaricidally effective amount of a composition comprising a synergistic mixture of 1 to 100 parts by weight of (S)α-cyano-3-phenoxy-benzyl 1R, cis 2,2-dimethyl-3-(2',2'-dibromovinyl)-cyclopropane-1-carboxylate and 100 parts by weight of 2,2,2-trichloro-1,1-di-(4-chlorophenyl)-ethanol.

7. The method of claim 6 wherein the composition is used at a rate of 10 to 1000 g per hectare.

8. The method of claim 6 wherein the composition is used at a rate of 200 to 450 g per hectare.

9. The method of claim 6 wherein the composition is used at a rate of 200 to 450 g per hectare.

10. The method of claim 6 wherein the composition is used at a rate of 15 to 500 g per hectare.

11. The method of claim 6 wherein the composition is used at a rate of 15 to 500 g per hectare.

UNITED STATES PATENT AND TRADEMARK OFFICE
CERTIFICATE OF CORRECTION

PATENT NO. : 4,357,350
DATED : November 2, 1982
INVENTOR(S) : JEAN J. HERVE ET AL.

It is certified that error appears in the above-identified patent and that said Letters Patent is hereby corrected as shown below:

Column 4, line 22: " % reduction = $(N_1-NF)/N_1 \times 100$" should read -- % reduction = $\dfrac{N_1-NF}{N_1} \times 100$ --.

Signed and Sealed this

First Day of March 1983

[SEAL]

Attest:

GERALD J. MOSSINGHOFF

Attesting Officer  Commissioner of Patents and Trademarks